United States Patent [19]  
Tsai et al.

[11] Patent Number: 4,626,209  
[45] Date of Patent: Dec. 2, 1986

[54] ORTHODONTIC BRACKET WITH METALLIC COATED BONDING BASE

[75] Inventors: Min H. Tsai, Van Nuys; John E. Sargeant, Los Alamitos, both of Calif.

[73] Assignee: Unitek Corporation, Monrovia, Calif.

[21] Appl. No.: 600,603

[22] Filed: Apr. 17, 1984

Related U.S. Application Data

[63] Continuation of Ser. No. 483,469, Apr. 11, 1983, abandoned.

[51] Int. Cl.⁴ .............................. A61C 3/00
[52] U.S. Cl. .......................... 433/9; 427/2; 427/423
[58] Field of Search ............ 433/8, 9; 427/2, 34, 427/423

[56] References Cited

U.S. PATENT DOCUMENTS

| | | | |
|---|---|---|---|
| 3,605,123 | 9/1971 | Hahn | 128/92 C |
| 3,775,850 | 12/1973 | Northcutt | 433/9 |
| 4,049,841 | 9/1977 | Coker et al. | 427/34 |
| 4,114,272 | 9/1978 | Saragossi | 427/423 |
| 4,145,764 | 3/1979 | Suzuki et al. | 427/2 |
| 4,243,386 | 1/1981 | Kawaguchi | 433/9 |
| 4,263,341 | 4/1981 | Martyniak | 427/423 |

Primary Examiner—John J. Wilson  
Attorney, Agent, or Firm—Richard H. Brink; Stuart E. Krieger; Elizabeth O. Slade

[57] ABSTRACT

An orthodontic bracket containing a thin metallic coating on the bracket base; the coating being applied onto the bracket base by thermally spraying a molten metallic powder.

1 Claim, 7 Drawing Figures

ORTHODONTIC BRACKET WITH METALLIC COATED BONDING BASE

This application is a continuation of U.S. application Ser. No. 06/483,469 filed 4/11/83, now abandoned.

BACKGROUND OF THE INVENTION

A. Field of the Invention

This invention relates generally to orthodontic appliances and more particularly to the base portion of orthodontic appliances involved in direct bonding to a tooth.

B. Description of Prior Art

The conventional method of orthodontic treatment has been through the use of metal brackets welded onto metal bands. The bands are mounted onto the tooth and an arch wire is connected to the brackets, so as to apply force to the tooth to properly position it within the dental arch. Problems arising from the use of bands include decalcification, patient discomfort and gingival irritation. Bandless brackets bonded directly to the tooth surface were made possible from experiments by Buonocore who etched tooth enamel with phosphoric acid to enhance the bonding of adhesives to the tooth (Journal of Dental Research, 34 (6) pp. 849-853, 1955).

A bandless bracket typically consists of two parts. One is the bracket body with grooves for accommodating the arch wire to transmit orthodontic force to the tooth. The other is the bracket base for supporting the bracket body and for bonding to the adhesive. Bandless brackets are made of metallic or plastic materials. Plastic is more aesthetically pleasing, however, plastic brackets are too soft and deform during treatment, and also may discolor rapidly in the oral environment. Stainless steel brackets provide strength to withstand the forces required for the treatment, but stainless steel brackets cannot be bonded effectively to the adhesive. To enhance the adhesion, Retief et al (American Journal of Orthodontics, 58 (1) p. 35, 1970) use brackets with slots in the bases to provide mechanical retention and to form a physical lock between the bracket base and adhesive. It is, however, labor intensive to produce these types of brackets.

It is also well known in the art to use bonding pads to produce mechanical interlocking with adhesive. Bonding pads are joined to the brackets by brazing, welding or sintering techniques. Brackets often are angulated on the bonding pads when joined and can be misaligend causing parts to be rejected and raising production costs. In addition, the combination of a bracket and bonding pads is relatively thick increasing the potential of oral irritation.

It is an object of the present invention to provide an orthodontic appliances having a novel base portion to facilitate bonding of the base portion to a tooth, without the above-described disadvantages.

SUMMARY OF THE INVENTION

This object is accomplished by projecting molten metallic particles onto the bonding surface of the base portion of stainless steel brackets to produce a surface with sufficient roughness to facilitate adhesive bonding.

Metallic molten powders which are non-toxic and corrosion resistant, are thermally sprayed onto the bonding surface of the base portion to produce a thin coating having asperities. These asperities facilitate direct bonding with an adhesive to the tooth surface. The bonding surface may have grooves or recesses for mechanical interlocking and/or increasing the area of that bond surface.

TABLE 1

| FIG. | Magnification | Thermally Sprayed Particle |
|---|---|---|
| 1 | 1100× | Titanium |
| 2 | 5500× | Titanium |
| 3 | 1100× | Titanium Carbide |
| 4 | 5500× | Titanium Carbide |
| 5 | 1100× | Type 304 Stainless Steel |
| 6 | 5500× | Type 304 Stainless Steel |

Figure 1:
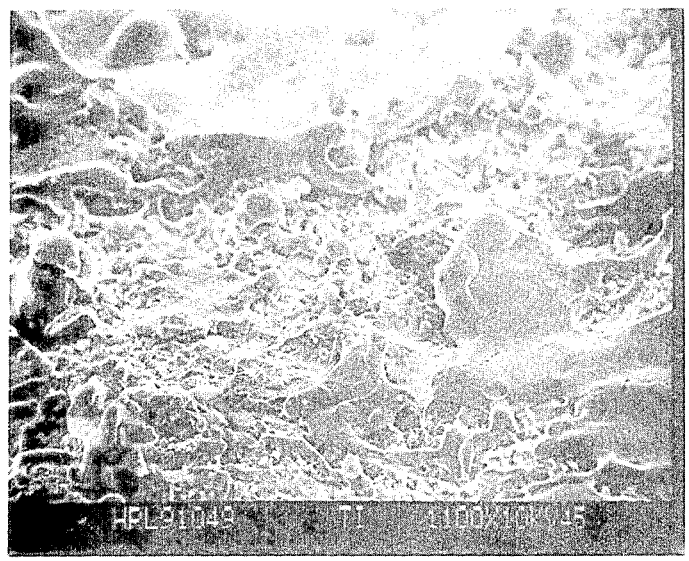
FIGS. 1–6, described in Table I below, are photomicrographs of a stainless steel support base coated with thermally sprayed particles, in accordance with the present invention.
Figure 2:
Figure 3:
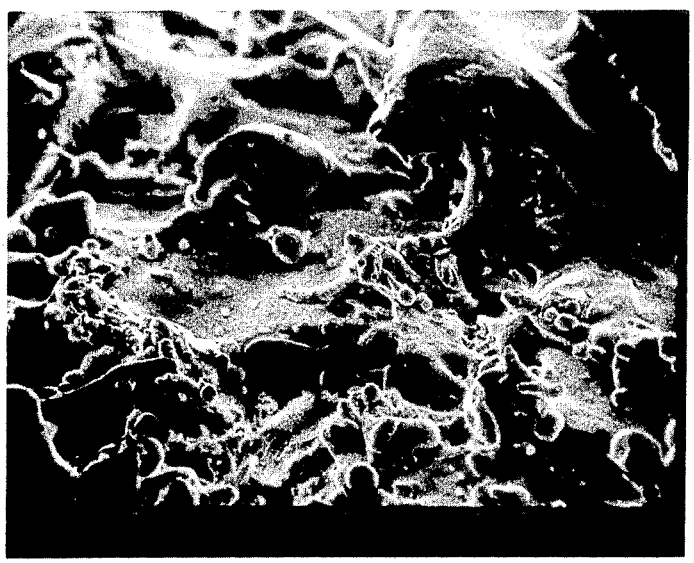
Figure 4:
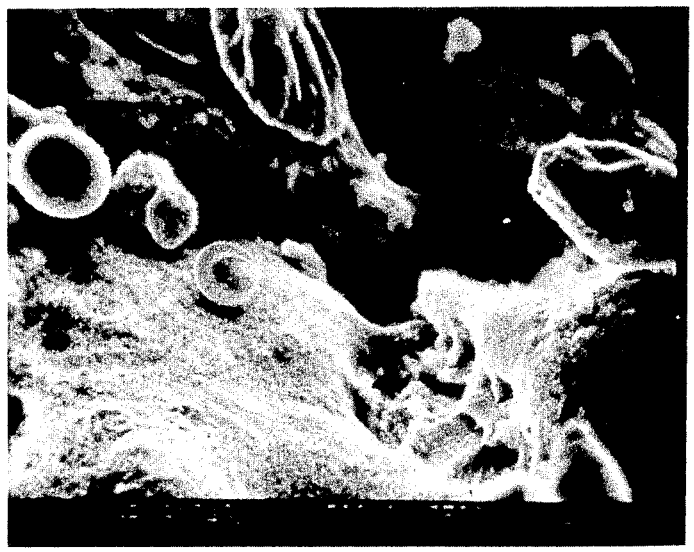
Figure 5:
Figure 6:
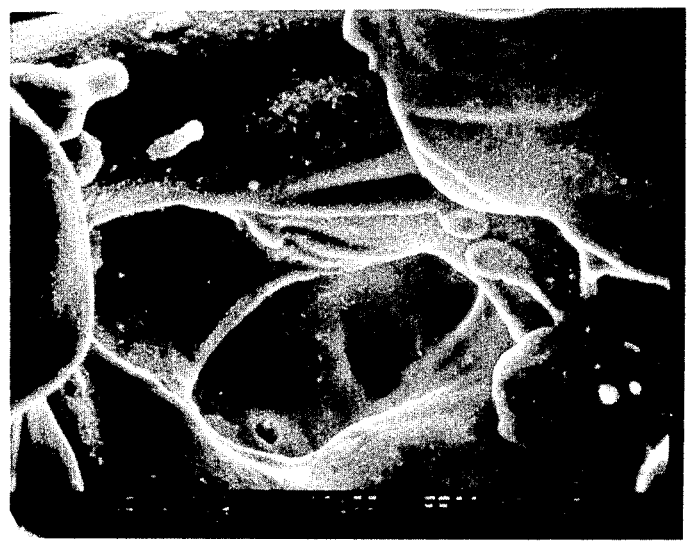
Figure 7:
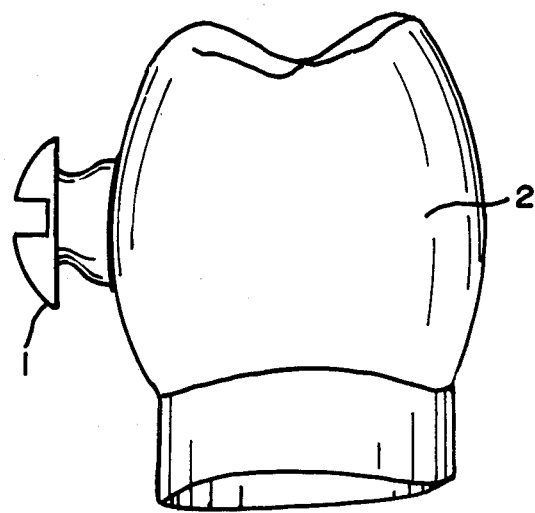

FIG. 7 is a side view of an orthodontic bracket with a molten particle spray coated base bonded to a tooth with an adhesive.

DESCRIPTION OF THE PREFERRED EMBODIMENTS

According to the instant invention a molten-particle spraying process is utilized to form a roughened surface on the base of an orthodontic bracket. Such a bracket is illustrated in FIG. 7. In particular the oxyacetylene flame process and the plasma flame process. These are processes well known in the art and described, for example, in the publication Ceramic Processing, pp. 105–111, National Academy of Sciences, Washington, D.C. 1968, in Nuclear Applications of Nonfissionable Ceramics, Boltax seq., and elsewhere in Flame Spray Handbook, vol. 111, "Plasma Flame Process" (Metco Ltd., 1965). The particles are melted then accelerated to a high speed to strike the substrate, whereupon they flatten and freeze onto the substrate. The use of ceramic particles is avoided because of potential toxicity. Ceramic engineers postulate that toxicity might be caused by the loss of stoichiometry of ceramic compounds, phase changes or reaction products of the elevated temperature reaction of the ceramic particles and metal substrate. The exact mechanism is still not known.

In this invention, only corrosion resistant metallic powders selected from the group consisting of stainless steel, nickel alloys, cobalt alloys, titanium and titanium carbide are utilized to coat the stainless steel bracket base. By adopting the disclosed thermal spraying methods, such as the oxyacetylene flame process or the plasma flame process, metallic particles are melted and impinged onto the bonding surface of the bracket base. As the molten particles freeze, they form an integral part of the bracket and they also create sufficient surface roughness to enhance adhesive bonding. The bracket (1) is then bonded to the tooth (2) as shown in FIG. 7.

Bond strength of the coated bracket to the tooth surface with adhesive was tested in an Instron machine. Anterior bovine teeth, in lieu of human teeth, were used in these tests. Anterior bovine teeth were removed from the mandible and mounted in acrylic blocks. These assemblies were cleaned with pumice and a rag wheel. After being rinsed and dried, 37% $H_3PO_4$ was applied and allowed to etch the teeth for 90 seconds. The assemblies were rinsed with water and after the etching period and all traces of moisture were removed with a heat gun. Care was taken to keep the temperature of the assemblies low enough to avoid damage to the teeth. After the teeth were prepared, a standard procedure used in an orthodontic office was followed to bond the coated bracket to the teeth using sealant and adhesive. After allowing the adhesive to cure, the bracket-tooth assemblies were immersed in water and kept at 37° C. for 18 to 24 hours. At the end of this period, the assemblies were removed from the water bath and mounted to the stationary holder of the Instron machine. The bracket-tooth assemblies were oriented to the proper place for the application of shear force. The bracket was attached to the crosshead by means of a loop of stainless steel wire. The crosshead was set to raise at a rate of 0.1 inch per minute. The scale was set at one pound per 0.1 inch and the chart was set at one inch per minute. Shear bond strength in pounds was recorded on the chart paper. The bond strengths obtained from coated brackets were compared with those of similar stainless steel brackets bonded to mesh pad. These stainless steel brackets are clinically used and commercially available. Superior bond strengths were observed with the coated brackets of the instant invention.

The following table lists the results obtained with the brackets prepared in accordance with the present invention:

EXAMPLES

| EXAMPLE | SPRAY PROCESS | ALLOY SYSTEM | PARTICLE SIZE ($\mu$) | BOND STRENGTH (lb) |
| --- | --- | --- | --- | --- |
| I | Oxyacetylene Flame | Nickel Alloy | 10–125 | 45.0 |
| II | Plasma/Flame | Nickel Alloy | 10–125 | 40.0 |
| III | Plasma/Flame | Stainless Steel 304 | 10–125 | 47.0 |
| IV | Plasma/Flame | Cobalt Alloy | 10–125 | 40.0 |

Bracket bonding bases of Examples I through IV produced by flame spray process—oxyacetylene and plasma—exhibit better bonds than mesh bonding pads. Bond strength of bracket with mesh pads is about 31 pounds. Coating of all these examples exhibit microscopic surface asperities which are essential for excellent bonding.

What is claimed is:

1. An orthodontic device comprising a stainless steel bracket having an integral bonding base with a thin coating having asperities, said coating being formed onto said bonding base by thermally sprayed molten corrosion resistant titanium carbide powder.

* * * * *